United States Patent
Naito et al.

(10) Patent No.: US 10,596,285 B2
(45) Date of Patent: Mar. 24, 2020

(54) STERILIZING METHOD

(71) Applicant: Ushio Denki Kabushiki Kaisha, Tokyo (JP)

(72) Inventors: Keisuke Naito, Tokyo (JP); Nobuyuki Hishinuma, Tokyo (JP); Shinji Suzuki, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 294 days.

(21) Appl. No.: 15/394,180

(22) Filed: Dec. 29, 2016

(65) Prior Publication Data

US 2018/0185531 A1 Jul. 5, 2018

(51) Int. Cl.
*A61L 2/00* (2006.01)
*A61L 2/20* (2006.01)

(52) U.S. Cl.
CPC ............ *A61L 2/202* (2013.01); *A61L 2/0023* (2013.01); *A61L 2202/11* (2013.01)

(58) Field of Classification Search
CPC ... A61L 2/24; A61L 2/202; A61L 2/10; A61L 2/03
USPC ........................................ 422/1, 24, 28, 305
See application file for complete search history.

(56) References Cited

U.S. PATENT DOCUMENTS

| | | | | |
|---|---|---|---|---|
| 4,427,636 A | * | 1/1984 | Obenshain | B01J 19/122 204/157.5 |
| 5,766,560 A | * | 6/1998 | Cole | B01J 19/088 422/186.07 |
| 5,928,607 A | * | 7/1999 | Frisk | A61L 2/10 422/24 |
| 2004/0202570 A1 | * | 10/2004 | Nadkarni | A61L 2/202 422/28 |
| 2005/0031486 A1 | * | 2/2005 | Mole | A61L 2/202 422/28 |
| 2011/0293484 A1 | | 12/2011 | Stausgaard et al. | |

(Continued)

FOREIGN PATENT DOCUMENTS

| | | |
|---|---|---|
| JP | H08-320399 A | 12/1996 |
| JP | H11-146905 A | 6/1999 |
| JP | 2000-245816 A | 9/2000 |

(Continued)

OTHER PUBLICATIONS

Extended European Search Report issued by the European Patent Office dated May 26, 2017, which corresponds to EP16002736.3-1370 and is related to U.S. Appl. No. 15/394,180.

(Continued)

*Primary Examiner* — Monzer R Chorbaji
(74) *Attorney, Agent, or Firm* — Studebaker & Brackett PC (57) ABSTRACT

Provided is a sterilization method capable of performing a sterilization treatment with high sterilization efficiency using ozone produced from an air regardless of the humidity of the air as an ozone raw material gas. In the sterilization method, the air as an ozone raw material gas is irradiated with light for producing ozone which does not include light with a wavelength region where the light decomposes ozone and which has a wavelength of not more than 200 nm to obtain an ozone-containing air, and an object to be sterilized is exposed to the ozone-containing air to sterilize the object. In the sterilization method, the relative humidity of the ozone raw material gas is not more than 60% RH.

16 Claims, 5 Drawing Sheets

(56) References Cited

U.S. PATENT DOCUMENTS

2014/0037499 A1* 2/2014 Shannon ................ A61L 2/202
  422/28

FOREIGN PATENT DOCUMENTS

| JP | 4697625 B2 | 6/2011 |
| JP | 2014-506496 A | 3/2014 |
| WO | 2012/103010 A1 | 8/2012 |

OTHER PUBLICATIONS

Puricare International, "Commercial Ozone Production and its application in irrigation systems and the Puricare Soilcare Unit", Jul. 29, 2014 (Jul. 29, 2014), XP055371760, Retrieved from the Internet: URL:http://www.puricare.co.za/UserFiles/12Annexure1PuricareProcessTrainingCoronaVsUltraVioletOzo.pdf [retrieved on May 11, 2017], 3 pgs.

An Office Action mailed by the Japanese Patent Office dated Oct. 8, 2019, which corresponds to Japanese Patent Application No. 2015-217420 and is related to U.S. Appl. No. 15/394,180.

* cited by examiner

STERILIZING METHOD

TECHNICAL FIELD

The present invention relates to a sterilization method using an ozone-containing air.

BACKGROUND ART

In a sterilization method, use of ozone ($O_3$) having high oxidation power is conventionally known.

Conventionally known examples of the production method may include a production method through electrical discharge and a production method through a photochemical reaction. In the method through electrical discharge, silent discharge such as creeping discharge is caused in an oxygen ($O_2$)-containing gas atmosphere to produce ozone. In the method through a photochemical reaction, an oxygen-containing gas is irradiated with an ultraviolet ray to produce ozone.

In the sterilization method, the production method of ozone through electrical discharge is widely used.

As a sterilization method using ozone, Patent Literature 1 discloses a technique in which an object to be sterilized which exists in an air constituting an atmosphere of a room or is attached to a surface of an object arranged in a room is exposed to a mixture of an ozone-containing air and a mist (moisture), subjecting the air constituting the atmosphere or the arranged object to a sterilization treatment.

In the sterilization method described in Patent Literature 1, the air constituting the atmosphere of the room is taken into a duct, and creeping discharge is caused in the duct to produce ozone. Then, an ozone-containing air which contains the produced ozone is mixed with a mist (moisture) which is discharged from an atomizing nozzle. Subsequently, a mixture of the ozone-containing air and the mist is supplied to the room from the duct. Asa result, the air constituting the atmosphere of the room and the arranged object in the room are subjected to a sterilization treatment. In this sterilization method, it is considered preferable that the humidity in the room where the mixture of the air containing ozone and the mist is supplied, that is, the humidity in the room where the sterilization treatment is performed is high, for example, not lower than 80% from the viewpoint of sterilization efficiency.

As described above, it is conventionally known that the sterilization efficiency in the sterilization method using ozone depends on an atmosphere in a space where an object to be sterilized is sterilized (a space in a room where the sterilization treatment is performed). However, it is not clear as to how a production method of ozone for use in the sterilization treatment affects the sterilization efficiency. A relationship between the production method of ozone and the sterilization efficiency has not been conventionally taken into consideration in the sterilization method using ozone.

CITATION LIST

Patent Literature

Patent Literature 1: Japanese Patent No. 4697625

SUMMARY OF INVENTION

Technical Problem to be Solved

The inventors of the present invention have intensively studied the sterilization method using ozone, and found that a state of a sterilization treatment varies depending on a production method of ozone for use in the sterilization treatment. Therefore, when an air is used as an ozone raw material gas in the sterilization method using ozone, the inventors have found that the humidity of the air may largely affect the sterilization efficiency in relation to the production method of ozone.

The present invention has been made in view of the foregoing circumstances and has as its object the provision of a sterilization method which is capable of performing a sterilization treatment with high sterilization efficiency using ozone produced from an air regardless of the humidity of the air that serves as an ozone raw material gas.

Means for Solving the Problems

The sterilization method according to the present invention is a sterilization method including: irradiating an air serving as an ozone raw material gas with light for producing ozone which does not include light with a wavelength region where the light decomposes ozone and which has a wavelength of not more than 200 nm, to obtain an ozone-containing air; and exposing an object to be sterilized to the ozone-containing air, thereby subjecting the object to a sterilization treatment, wherein the ozone raw material gas has a relative humidity of not more than 60% RH.

In the sterilization method of the present invention, it is preferable that the object to be sterilized exists in an opened space and the ozone is contained in the opened space in a concentration of not more than 100 ppm.

In the sterilization method of the present invention, it is preferable that the object to be sterilized is exposed to the ozone-containing air by supplying the ozone-containing air to a space where the object to be sterilized exists, with the ozone-containing air obtained by irradiating the ozone raw material gas with the light for producing ozone in a space where ozone is produced.

Further, it is preferable that the space where ozone is produced is partitioned within the space where the object to be sterilized exists. Moreover, it is preferable that an air constituting an atmosphere of the space where the object to be sterilized exists is supplied as the ozone raw material gas in the space where ozone is produced.

Advantageous Effects of Invention

In the sterilization method of the present invention, the object to be sterilized is exposed to the ozone-containing air which is obtained by irradiating the air serving as the ozone raw material gas with the light for producing ozone which does not include light with a wavelength region where the light decomposes ozone and which has a wavelength of not more than 200 nm. Therefore, the produced ozone is not decomposed due to irradiation with the light for producing ozone, and the sterilization efficiency is not largely affected by the humidity of the ozone raw material gas.

According to the sterilization method of the present invention, a sterilization treatment can be performed with high sterilization efficiency using ozone produced from an air regardless of the humidity of the air that is the ozone raw material gas. Accordingly, in the sterilization method of the present invention, the sterilization treatment can be performed with high sterilization efficiency using an ambient air as the ozone raw material gas even under a low humidity environment.

DESCRIPTION OF EMBODIMENTS

Hereinafter, embodiments of the sterilization method of the present invention will be described.

In the sterilization method of the present invention, examples of the object which is subjected to a sterilization treatment may include an air constituting an atmosphere of a space (room space) in a hospital (for example, sickroom), a factory (for example, food-handling room) or a food warehouse, water and an arranged object such as a chair and a medical equipment. Such an object to be sterilized which exists in an air or water or is attached to a surface of the arranged object in the room is sterilized by the sterilization method of the present invention.

In the sterilization method of the present invention, an ozone raw material gas which is an air (hereinafter also referred to as "raw material air") is irradiated with light for producing ozone to obtain an ozone-containing air, and the object to be sterilized is exposed to the obtained ozone-containing air to sterilize the object to be sterilized. The light for producing ozone is characterized by not including light with a wavelength region where the light decomposes ozone and having a wavelength of not more than 200 nm (ultraviolet ray).

Herein, the "light with a wavelength region where the light decomposes ozone" is light with a wavelength of 240 to 280 nm (ultraviolet ray).

In the sterilization method of the present invention, the wavelength region of the light for producing ozone is not more than 200 nm, and preferably includes 172 nm.

Since the light for producing ozone is light with a wavelength of not more than 200 nm, oxygen constituting the raw material air is decomposed to produce ozone. Specifically, when oxygen molecules are irradiated with the light for producing ozone, the oxygen molecules are decomposed (dissociated) to generate oxygen atoms, and each of the oxygen atoms is bonded to another oxygen molecule to produce ozone. In addition, since the light for producing ozone is light with a wavelength of not more than 200 nm, no irradiation with light with a wavelength region where the light decomposes ozone occurs. Therefore, produced ozone is not decomposed due to the irradiation with the light for producing ozone.

Since the light for producing ozone includes light with a wavelength of 172 nm, hydrogen peroxide ($H_2O_2$) which is one kind of active oxygen can be produced with high efficiency by irradiating the raw material air with the light for producing ozone. For this reason, high sterilization efficiency can be achieved.

As the raw material air, an air constituting an external atmosphere of a space where the object to be sterilized exists or an air constituting the space where the object to be sterilized exists may be suitably used.

In the sterilization method of the present invention, a condition of irradiating the raw material air with the light for producing ozone is appropriately determined in consideration of the kind of the object to be sterilized, the kind of the object which is subjected to a sterilization treatment and a sterilization ratio required for the object which is subjected to a sterilization treatment.

In an example of the condition of irradiating the raw material air with the light for producing ozone, the radiant intensity is 23.3 $mW/cm^2$, and the irradiation time is 14.6 msec.

In the sterilization method of the present invention, it is preferable that the ozone-containing air obtained by irradiating the raw material air with the light for producing ozone is immediately used for the sterilization treatment from the viewpoint of sterilization efficiency.

In the sterilization method of the present invention, an exposure time of the object to be sterilized to the ozone-containing air, that is, a sterilization treatment time is appropriately determined depending on the ozone concentration of the ozone-containing air and in consideration of the kind of the object to be sterilized, the kind of the object which is subjected to a sterilization treatment and a sterilization ratio required for the object which is subjected to a sterilization treatment. It is preferable that a CT value is not lower than 60 from the viewpoint of relation to the ozone concentration in the ozone-containing air. The CT value is calculated by product of the ozone concentration (ppm) and the exposure time (min).

Herein, the "CT value" is an indication exhibiting a sterilization/inactivation effect. A higher CT value represents a higher sterilization/inactivation effect.

In the sterilization method of the present invention, an ozone-producing light source for emitting the light for producing ozone emits light with a wavelength of not more than 200 nm, but does not emit light with a wavelength region where the light decomposes ozone. Specifically, a discharge lamp such as an excimer lamp and a rare-gas fluorescent lamp, or a light-emitting element such as an LED element and an LD element is used.

When an excimer lamp or a rare-gas fluorescent lamp is used as the ozone-producing light source, supply of larger electric power is not required to generate a large amount of ozone as compared with a mercury lamp. For this reason, ozone may be produced with high efficiency.

Alternatively, when an LED element is used as the ozone-producing light source, a plurality of LED elements may be appropriately arranged on a heat dissipating substrate.

Herein, the "excimer lamp" is a lamp that utilizes discharge (dielectric barrier discharge) generated by applying a high frequency voltage of 50 Hz to several MHz through a dielectric, as described in Kogelschatz, Pure & Appl. Chem. Vol. 62, No. 9, 1990, pp. 1667 to 1674.

An example of the "rare-gas fluorescent lamp" is one having a cylindrical light-emitting tube which has sealing portions on both ends and is made of a dielectric material having light transparency, such as quartz glass. In the light-emitting tube, a rare gas such as xenon, argon or krypton is sealed, and a phosphor layer is formed on an inner circumferential surface of the light-emitting tube. A pair of external electrodes is provided to the light-emitting tube to be separated from each other in a tube axial direction of the light-emitting tube. In such a rare-gas fluorescent lamp, when a high frequency voltage is applied to the pair of external electrodes, discharge occurs between the pair of external electrodes with the dielectric (tube wall of the light-emitting tube made of quartz glass) interposed therebetween. As a result, a rare-gas excimer is formed inside the light-emitting tube. When the rare-gas excimer is transferred to a ground state, excimer light is emitted. A phosphor constituting the phosphor layer is excited by this excimer light, to generate an ultraviolet ray from the phosphor layer. The ultraviolet ray is emitted toward the outside of the light-emitting tube.

As specific preferable examples of the ozone-producing light source, a xenon excimer lamp having a center wavelength of 172 nm may be mentioned.

Figure 1:
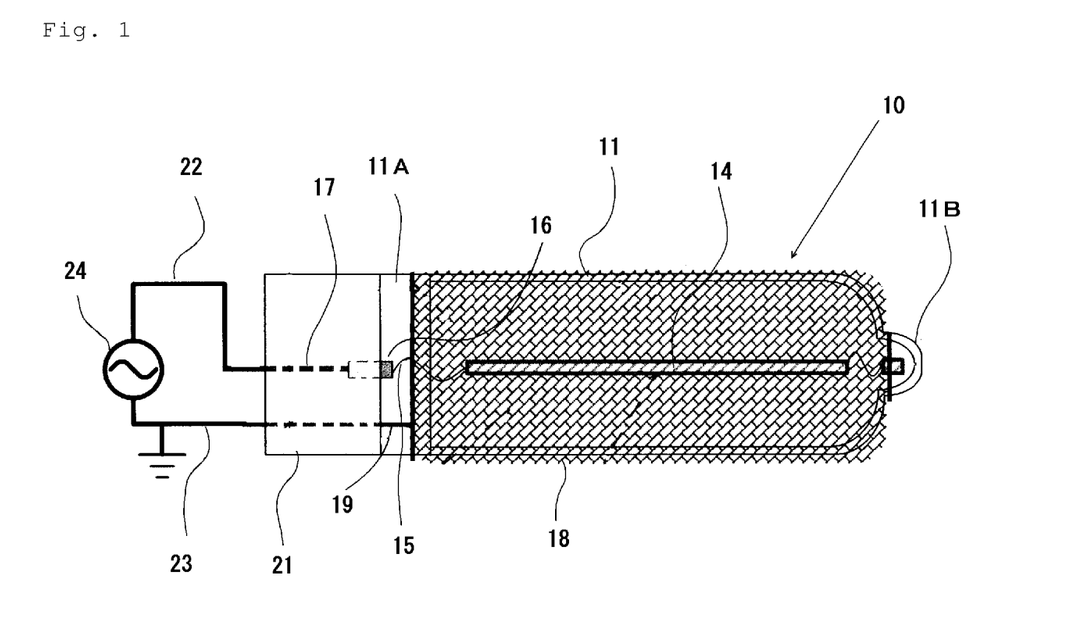
FIG. 1 is an explanatory view illustrating one example of a configuration of an excimer lamp used in a sterilization method of the present invention with a base member and a high frequency power supply.

As shown in FIG. 1, an excimer lamp 10 includes a right-circular-cylindrical light-emitting tube 11. The light-emitting tube 11 is made of, for example, an ultraviolet ray-transmissive material such as quartz glass. One end (right end in FIG. 1) of the light-emitting tube 11 is sealed and the other end thereof is formed to have a flat sealing portion 11A by a pinch sealing process. In the light-emitting tube 11, a rare gas such as xenon is sealed. Further, a coil-shaped internal electrode 14 is disposed so as to extend along the tube axis of the light-emitting tube 11. The internal electrode 14 is electrically connected to a metal foil 16 buried in the sealing portion 11A through an internal lead 15. The metal foil 16 is electrically connected to an external lead 17 for an internal electrode at one end thereof, where the external lead 17 projects from an outer end surface of the sealing portion 11A to the outside. On a circumference surface of the light-emitting tube 11, a net-shaped external electrode 18 is provided. The external electrode 18 is electrically connected to an external lead 19 for an external electrode at one end thereof, where the external lead 19 extends along the sealing portion 11A. A light-emitting region is formed at a region where the internal electrode 14 and the external electrode 18 are opposed to each other through an internal space of the light-emitting tube 11 and a tube wall of the light-emitting tube 11. Thus, a discharge space is formed in the light-emitting tube 11.

To the sealing portion 11A of the excimer lamp 10, a base member 21 made of ceramic is attached. Feeder wires 22 and 23 are disposed in the base member 21, and are connected to the other end of the external lead 17 for an internal electrode and the other end of the external lead 19 for an external electrode, respectively.

In the excimer lamp 10, the internal electrode 14 is connected to a high frequency power supply 24 through the metal foil 16, the external lead 17 for an internal electrode and the feeder wire 22 of the base member 21, and the external electrode 18 is grounded through the external lead 19 for an external electrode and the feeder wire 23 of the base member 21.

In the example of FIG. 1, the light-emitting tube 11 has an exhaust duct remaining portion 11B on one end.

As specific examples of the sterilization method of the present invention, techniques using various sterilization treatment mechanisms described below may be mentioned.

A sterilization treatment mechanism is appropriately selected and used in consideration of the kind of the object which is subjected to a sterilization treatment and a sterilization ratio required for the object which is subjected to a sterilization treatment.

Figure 2:
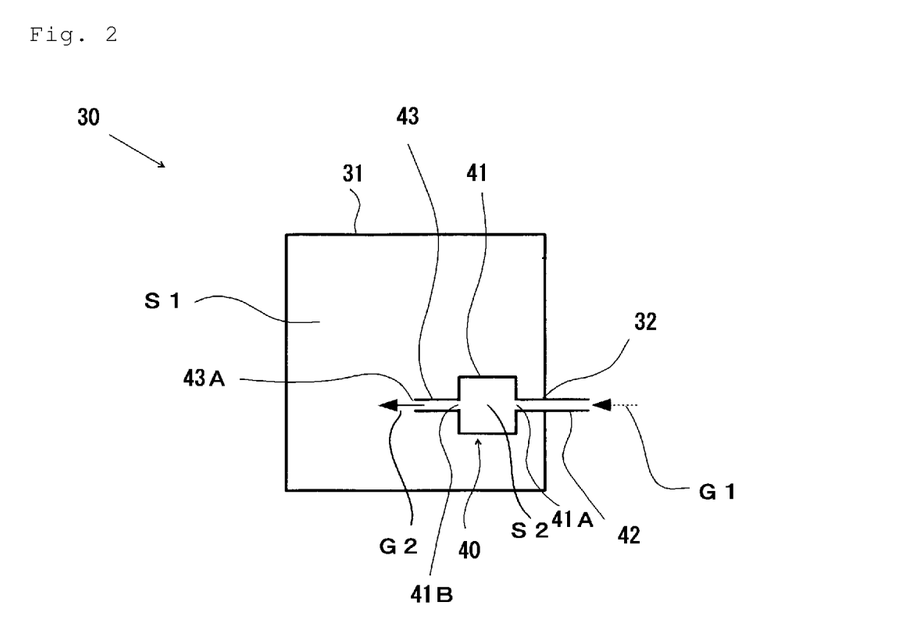
FIG. 2 is an explanatory view illustrating one example of a configuration of a sterilization treatment mechanism used to perform the sterilization method of the present invention.
Figure 3:
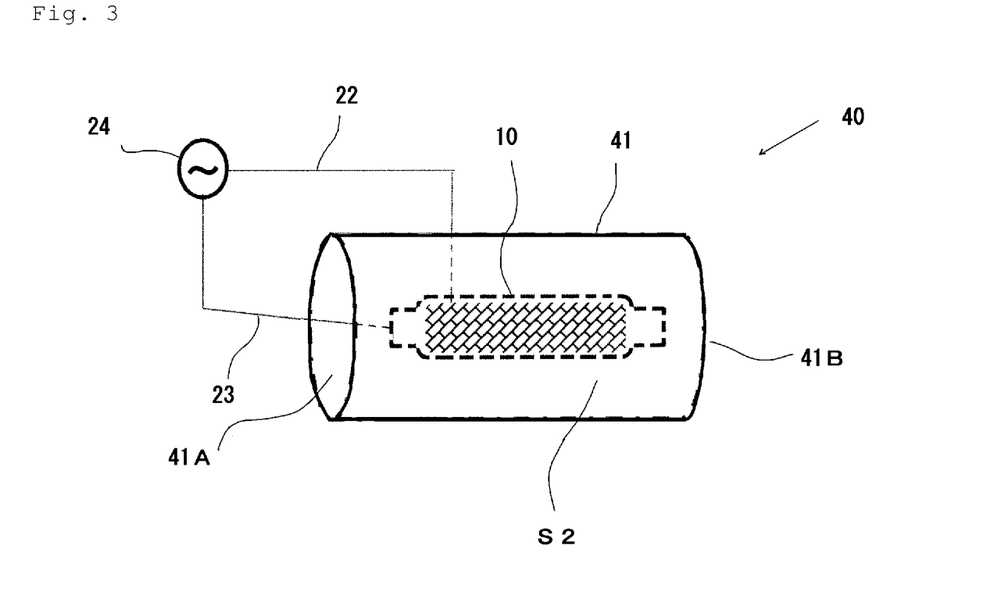
FIG. 3 is an explanatory view illustrating an outline of one example of a configuration of an ozone generator in the sterilization treatment mechanism of FIG. 2.

First Sterilization Treatment Mechanism:

FIG. 2 is an explanatory view illustrating one example of a configuration of a sterilization treatment mechanism used to perform the sterilization method of the present invention. FIG. 3 is an explanatory view illustrating an outline of one example of a configuration of an ozone generator in the sterilization treatment mechanism of FIG. 2.

In a first sterilization treatment mechanism 30, a space S1 where an object to be sterilized exists is an object which is subjected to a sterilization treatment. The space S1 is surrounded by a partition 31 which is formed of a box member having a cubic external appearance. In the first sterilization treatment mechanism 30, a space S2 where ozone is produced is partitioned within the space S1.

In the first sterilization treatment mechanism 30, for example, the space S2 where ozone is produced in an ozone generator 40 is disposed in the space S1 where an object to be sterilized exists and which is a space in a room such as a sickroom in a hospital, a food-handling room in a factory and a food warehouse. In the first sterilization treatment mechanism 30, a sterilization treatment is performed in a state where the space S1 where an object to be sterilized exists is a closed space, that is, a state where an openable and closable opening portion (for example, door or window) which connects the room space (space S1) to the outside (the outside of the partition 31) is closed.

When a raw material air G1 is irradiated with light for producing ozone, oxygen in the raw material air G1 absorbs the light for producing ozone, so that the ozone generator 40 produces ozone. The ozone generator 40 discharges an ozone-containing air G2 containing the produced ozone outside the ozone generator 40.

The ozone generator 40 is provided with an elongated right-circular-cylindrical air flow channel forming member 41. The partition that divides into the space S1 where an object to be sterilized exists and the space S2 where ozone is produced is constituted by the air flow channel forming member 41. Specifically, the space S2 where ozone is produced is constituted by a cylindrical internal space of the air flow channel forming member 41. The air flow channel forming member 41 has an air inlet 41A on one end and an air outlet 41B on another end. The air inlet 41A is connected to a raw material air supply unit (not shown) provided in the outside of the space S1 where an object to be sterilized exists, that is, the outside of the partition 31 through a raw material air channel formed from a right-circular-cylindrical air introducing channel forming member 42. The partition 31 has an opening for air supply 32. The air introducing channel forming member 42 is air-tightly inserted into the opening for air supply 32. The air outlet 41B is connected to a right-circular-cylindrical air leading channel forming member 43. An air outlet 43A in the air leading channel forming member 43 is positioned at a substantially center of the space S1. In the air flow channel forming member 41 (space S2 where ozone is produced), an ozone-producing light source including the excimer lamp 10 having the construction shown in FIG. 1 is disposed so that the whole light-emitting region is positioned inside of the air flow channel forming member 41 while the light source is connected to the high frequency power supply 24 through the feeder wire 22 and grounded through the feeder wire 23. The excimer lamp 10 has an outside diameter which is smaller than the internal diameter of the air flow channel forming member 41, and a light-emitting length (length of the light-emitting region) which is shorter than the whole length of the air flow channel forming member 41. The excimer lamp 10 is supported by a supporting member (not shown) so that the tube axis of the excimer lamp 10 (lamp central axis) substantially coincides with the tube axis of the air flow channel forming member 41 in the air flow channel forming member 41. Specifically, the excimer lamp 10 is disposed so that the tube axis (lamp central axis) substantially coincides with the tube axis of the air flow channel forming member 41 and the whole circumference surface of the excimer lamp 10 is spaced apart from the inner circumferential surface of the air flow channel forming member 41 to form a circular space between the circumference surface and the inner circumferential surface. Thus, in the air flow channel forming member 41, that is, in the space S2 where ozone is produced, an air flow channel in which the raw material air G1 supplied from the raw material air supply unit through the air inlet 41A flows toward the air outlet 41B is formed.

The whole inner circumferential surface of the air flow channel forming member 41 has resistance to ozone and if necessary, light-shielding property against light from the ozone-producing light source (excimer lamp 10). It is preferable that the air flow channel forming member 41 is made of a material having resistance to ozone such as a fluorocarbon resin and stainless steel.

It is preferable that at least a region which is irradiated with the light from the ozone-producing light source (excimer lamp 10) in the inner circumferential surface of the air flow channel forming member 41 has light reflectivity against the light for producing ozone.

Since the air flow channel forming member 41 has light reflectivity at the region which is irradiated with the light from the ozone-producing light source (excimer lamp 10), the light from the ozone-producing light source (light for producing ozone) may be effectively utilized. Therefore, ozone may be produced with higher efficiency.

Since the air flow channel forming member 41 is made of a metal (for example, aluminum) in the example of the drawings, the whole inner circumferential surface has resistance to ozone, light reflectivity and light-shielding property against the light from the excimer lamp 10.

As the raw material air supply unit, for example, an air blowing unit is used. Such an air blowing unit is capable of introducing an air (ambient air) constituting an external atmosphere from the outside of the partition 31 and supplying and flowing the air constituting the external atmosphere to the inside (space S2) of the air flow channel forming member 41.

A condition of supplying the raw material air G1 by the raw material air supply unit is appropriately determined in consideration of the internal diameter of the air flow channel forming member 41 and the outside diameter of the excimer lamp 10 so that the raw material air G1 is irradiated with the light for producing ozone in the air flow channel forming member 41 (space S2 where ozone is produced) under a desired irradiation condition.

In the first sterilization treatment mechanism 30 with such a configuration, a sterilization treatment of sterilizing an object to be sterilized in the space S1 where the object to be sterilized exists is performed by the sterilization method of the present invention.

Specifically, in the ozone generator 40, the air (ambient air) constituting the external atmosphere of the partition 31 is supplied as the raw material air G1 to the inside (space S2 where ozone is produced) of the air flow channel forming member 41 through the air inlet 41A by the raw material air supply unit. The raw material air G1 supplied to the inside of the air flow channel forming member 41 flows in the air flow channel toward the air outlet 41B. At that time, the raw material air G1 is irradiated with the light (light for producing ozone) from the excimer lamp 10 (ozone-producing light source). As a result, oxygen in the raw material air G1 absorbs the light for producing ozone (ultraviolet ray) resulting in an ozone production reaction. Thus, ozone is produced. The ozone-containing air G2 which contains the ozone produced by this irradiation of the raw material air G1 with the light for producing ozone is discharged outside the ozone generator 40 from the air outlet 43A through the air outlet 41B. Thus, the object to be sterilized in the space S1 where the object to be sterilized exists is exposed to the ozone-containing air G2 which is supplied to the space S1 from the space S2 where the ozone is produced. Therefore, the space S1 is subjected to a sterilization treatment.

Figure 4:
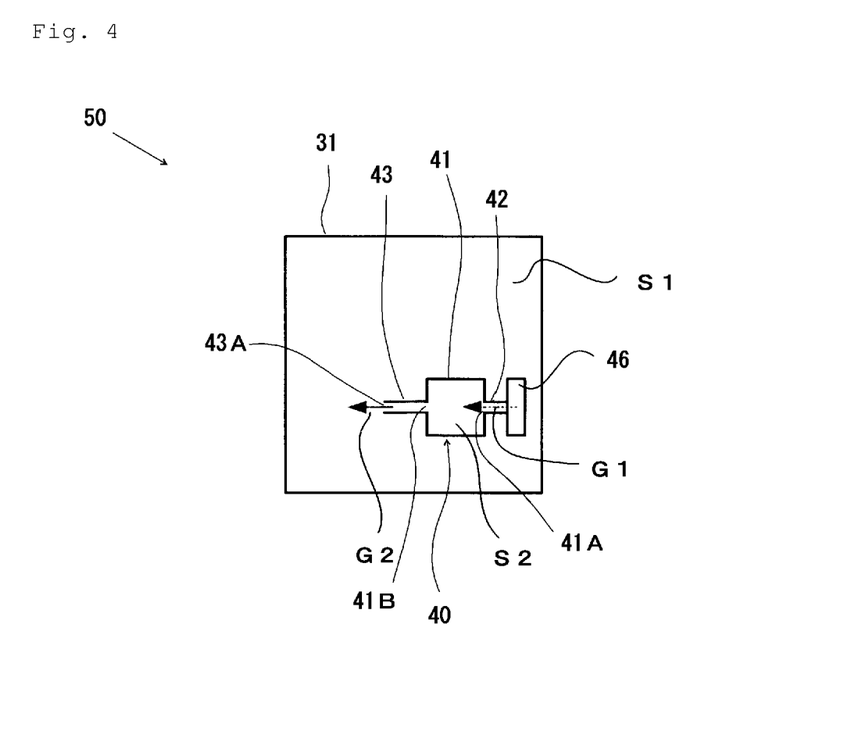
FIG. 4 is an explanatory view illustrating another example of the configuration of the sterilization treatment mechanism used to perform the sterilization method of the present invention.

Second Sterilization Treatment Mechanism:

FIG. 4 is an explanatory view illustrating another example of the configuration of the sterilization treatment mechanism used to perform the sterilization method of the present invention.

A second sterilization treatment mechanism 50 has the same configuration as that of the first sterilization treatment mechanism 30 according to FIG. 2 except that, in the first sterilization treatment mechanism 30 according to FIG. 2, the raw material air supply unit is provided in the space S1 where the object to be sterilized exists, i.e., in the space S1 which is surrounded by the partition 31, and the partition 31 does not have the opening for air supply 32. Specifically, the second sterilization treatment mechanism 50 is configured so that the air constituting the atmosphere of the space S1 where the object to be sterilized exists is supplied as the raw material air G1 to the inside (space S2 where ozone is produced) of the air flow channel forming member 41.

In the second sterilization treatment mechanism 50, a raw material air supply unit 46 configured to circulate the air constituting the atmosphere of the space S1 where the object to be sterilized exists is used. Specifically, the raw material air supply unit 46 used in this example can introduce the air constituting the atmosphere of the space S1 where the object to be sterilized exists and supply and flow the air as the raw material air G1 to the inside (space S2 where ozone is produced) of the air flow channel forming member 41.

The second sterilization treatment mechanism 50 is configured, for example, so that the space S2 where ozone is produced in the ozone generator 40 is disposed in the space S1 where the object to be sterilized exists which is a space in a room such as a sickroom in a hospital, a food-handling room in a factory and a food warehouse. In the second sterilization treatment mechanism 50, a sterilization treatment is performed in a state where the space S1 where the object to be sterilized exists is a closed space, that is, a state where an openable and closable opening portion (for example, door or window) which connects the room space (space S1) to the outside (the outside of the partition 31) is closed.

In the second sterilization treatment mechanism 50 with such a configuration, a sterilization treatment of sterilizing an object to be sterilized in the space S1 where the object to be sterilized exists is performed by the sterilization method of the present invention.

Specifically, in the ozone generator 40, the air constituting the atmosphere of the space S1 where the object to be sterilized exists is supplied as the raw material air G1 to the inside (space S2 where ozone is produced) of the air flow channel forming member 41 through the air inlet 41A by the raw material air supply unit 46. The raw material air G1 supplied to the inside of the air flow channel forming member 41 flows in the air flow channel toward the air outlet 41B. At that time, the raw material air G1 is irradiated with the light (light for producing ozone) from the excimer lamp 10 (ozone-producing light source). As a result, oxygen in the raw material air G1 absorbs the light for producing ozone (ultraviolet ray) resulting in an ozone production reaction. Thus, ozone is produced. The ozone-containing air G2 which contains the ozone produced by this irradiation of the raw material air G1 with the light for producing ozone is discharged outside the ozone generator 40 from the air outlet 43A through the air outlet 41B. Thus, the object to be sterilized in the space S1 where the object to be sterilized exists is exposed to the ozone-containing air G2 which is supplied to the space S1 from the space S2 where the ozone is produced. Therefore, the space S1 is subjected to a sterilization treatment.

Figure 5:
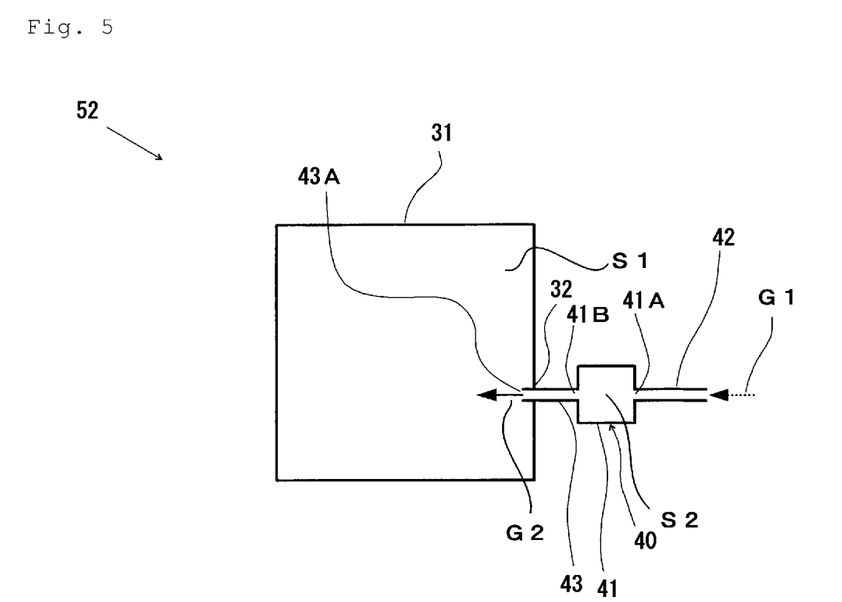
FIG. 5 is an explanatory view illustrating further another example of the configuration of the sterilization treatment mechanism used to perform the sterilization method of the present invention.

Third Sterilization Treatment Mechanism:

FIG. 5 is an explanatory view illustrating further another example of the configuration of the sterilization treatment mechanism used to perform the sterilization method of the present invention.

A third sterilization treatment mechanism 52 has the same configuration as that of the first sterilization treatment mechanism 30 according to FIG. 2 except that, in the first sterilization treatment mechanism 30 according to FIG. 2, the space S2 where ozone is produced is disposed outside the space S1 where the object to be sterilized exists, specifically, the ozone generator 40 is disposed outside the space S1, that is, outside of the partition 31.

In the third sterilization treatment mechanism 52, the air leading channel forming member 43 is tightly inserted into the opening for air supply 32 of the partition 31.

The third sterilization treatment mechanism 52 is configured, for example, so that the ozone generator 40 is disposed outside the space S1 where the object to be sterilized exists which is a space in a room such as a sickroom in a hospital, a food-handling room in a factory and a food warehouse. In the third sterilization treatment mechanism 52, a sterilization treatment is performed in a state where the space S1 where the object to be sterilized exists is a closed space, that is, a state where an openable and closable opening portion (for example, door or window) which connects the room space (space S1) to the outside (the outside of the partition 31) is closed.

In the third sterilization treatment mechanism 52 with such a configuration, a sterilization treatment of sterilizing an object to be sterilized in the space S1 where the object to be sterilized exists is performed by the sterilization method of the present invention.

Specifically, in the ozone generator 40, the air (ambient air) constituting the external atmosphere of the partition 31 is supplied as the raw material air G1 to the inside (space S2 where ozone is produced) of the air flow channel forming member 41 through the air inlet 41A by the raw material air supply unit. The raw material air G1 supplied to the inside of the air flow channel forming member 41 flows in the air flow channel toward the air outlet 41B. At that time, the raw material air G1 is irradiated with the light (light for producing ozone) from the excimer lamp 10 (ozone-producing light source). As a result, oxygen in the raw material air G1 absorbs the light for producing ozone (ultraviolet ray) resulting in an ozone production reaction. Thus, ozone is produced. The ozone-containing air G2 which contains the ozone produced by this irradiation of the raw material air G1 with the light for producing ozone is discharged outside of the ozone generator 40 from the air outlet 43A through the air outlet 41B. Thus, the object to be sterilized in the space S1 where the object to be sterilized exists is exposed to the ozone-containing air G2 which is supplied to the space S1 from the space S2 where the ozone is produced. Therefore, the space S1 is subjected to a sterilization treatment.

Figure 6:
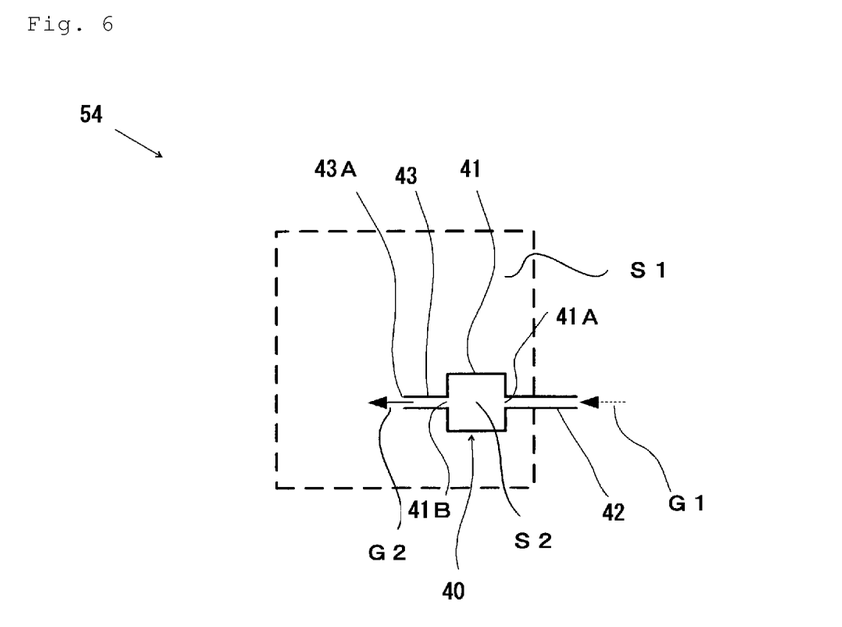
FIG. 6 is an explanatory view illustrating still another example of the configuration of the sterilization treatment mechanism used to perform the sterilization method of the present invention.

Fourth Sterilization Treatment Mechanism:

FIG. 6 is an explanatory view illustrating still another example of the configuration of the sterilization treatment mechanism used to perform the sterilization method of the present invention.

A fourth sterilization treatment mechanism 54 has the same configuration as that of the first sterilization treatment mechanism 30 according to FIG. 2 except that, in the first sterilization treatment mechanism 30 according to FIG. 2, a part or all of the partition 31 is not provided and the space S1 where the object to be sterilized exists is an opened space.

The fourth sterilization treatment mechanism. 54 is configured, for example, so that the space S2 where ozone is produced in the ozone generator 40 is disposed in the space S1 where the object to be sterilized exists which is a space in a room such as a sickroom in a hospital, a food-handling room in a factory and a food warehouse. In the fourth sterilization treatment mechanism 54, a sterilization treatment is performed in a state where the space S1 where the object to be sterilized exists is the opened space, that is, a state where an openable and closable opening portion (for example, door or window) which connects the room space (space S1) to the outside (the outside of the partition 31) is opened.

In the fourth sterilization treatment mechanism 54 with such a configuration, a sterilization treatment of sterilizing an object to be sterilized in the space S1 where the object to be sterilized exists is performed by the sterilization method of the present invention.

Specifically, in the ozone generator 40, the air (ambient air) constituting the external atmosphere of the space S1 where the object to be sterilized exists (provided that it is in communication with the space S1) is supplied as the raw material air G1 to the inside (space S2 where ozone is produced) of the air flow channel forming member 41 through the air inlet 41A by the raw material air supply unit. The raw material air G1 supplied to the inside of the air flow channel forming member 41 flows in the air flow channel toward the air outlet 41B. At that time, the raw material air G1 is irradiated with the light (light for producing ozone) from the excimer lamp 10 (ozone-producing light source). As a result, oxygen in the raw material air G1 absorbs the light for producing ozone (ultraviolet ray) resulting in an ozone production reaction. Thus, ozone is produced. The ozone-containing air G2 which contains the ozone produced by this irradiation of the raw material air G1 with the light for producing ozone is discharged outside the ozone generator 40 from the air outlet 43A through the air outlet 41B.

Thus, the object to be sterilized in the space S1 where the object to be sterilized exists is exposed to the ozone-containing air G2 which is supplied to the space S1 from the space S2 where the ozone is produced. Therefore, the space S1 is subjected to a sterilization treatment.

In the sterilization method of the present invention achieved by such a sterilization treatment mechanism, an object to be sterilized is exposed to the ozone-containing air which is obtained by irradiating the raw material air with the light for producing ozone. Therefore, the produced ozone is not decomposed due to irradiation with the light for producing ozone. As is apparent from experimental examples described below, the sterilization efficiency is not largely affected by the humidity of the raw material air unlike the case where an ozone-containing air obtained by silent discharge in the atmosphere of the raw material air is used. Specifically, high sterilization effect cannot be obtained with an air having a relative humidity of not more than 60% RH in a sterilization method using an ozone-containing air obtained by silent discharge in an atmosphere of a raw material air, and particularly, an air having a relative humidity of 20% RH cannot achieve sterilization efficiency. Even when such an air having a relative humidity of not more than 60% RH, in particular, an air having a relative humidity of 20% RH, is used as a raw material air, high sterilization efficiency can be achieved by the sterilization method of the present invention.

According to the sterilization method of the present invention, a sterilization treatment can be performed with high sterilization efficiency using ozone produced from an air regardless of the humidity of the air constituting the ozone raw material gas. As a result, in the sterilization method of the present invention, a sterilization treatment may be reliably performed with high sterilization efficiency even under a lower humidity environment, particularly under a lower humidity condition where the relative humidity is not more than 60% RH, preferably not more than 40% RH, further preferably 20% RH.

In the sterilization method of the present invention, the ozone concentration of the ozone-containing air can be easily controlled by adjusting the irradiation time of the raw material air with the light for producing ozone, or the like. Therefore, the ozone concentration in the space S1 where an object to be sterilized exists can be a concentration of not more than 100 ppm, preferably a concentration which does not adversely affect the human body, for example, not more than 50 ppm. In particular, when the space S1 where an object to be sterilized exists is an opened space like the fourth sterilization treatment mechanism 54, the ozone concentration in the space S1 may preferably be a concentration of not more than 50 ppm in consideration of adverse influence on the human body.

Therefore, the sterilization method of the present invention can suitably be used for a sterilization treatment of a living space which is a closed space or an opened space formed by opening or closing a door or a window.

The sterilization method of the present invention has been specifically described above. However, the present invention is not limited to the examples described above, and may be variously modified.

For example, a sterilization treatment mechanism used to perform the sterilization method of the present invention is not limited to the configuration described above (for example, the first sterilization treatment mechanism 30, the second sterilization treatment mechanism 50, the third sterilization treatment mechanism 52 and the fourth sterilization treatment mechanism 54).

Herein, experimental examples of the present invention will be described.

Experimental Example 1

Figure 7:
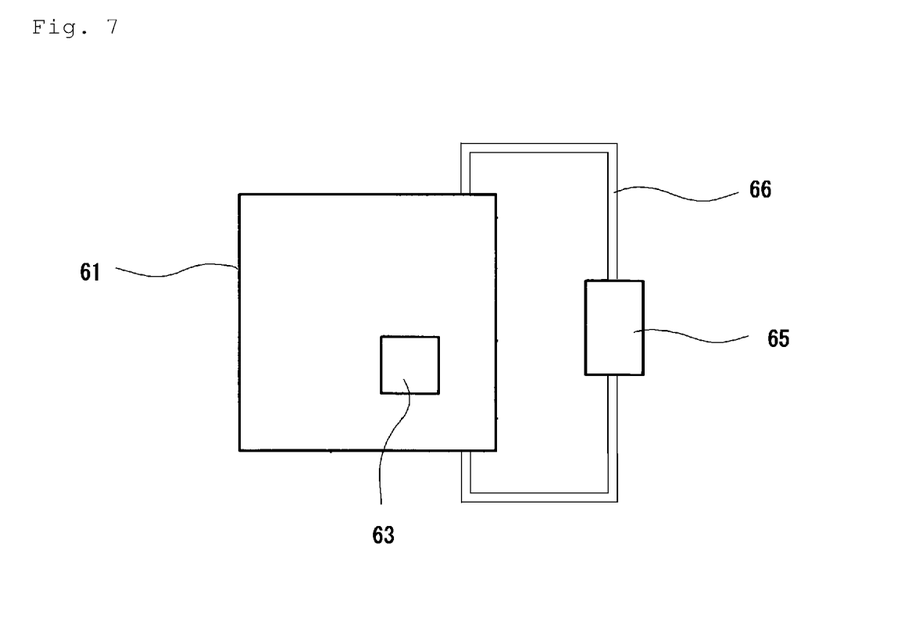
FIG. 7 is an explanatory view illustrating an outline of a configuration of a sterilization treatment mechanism used in Experimental Example 1.

A sterilization treatment mechanism for experiment (hereinafter referred to as "sterilization treatment mechanism for experiment (1)") provided with a 288-L environmental tester 61, an ozone generator 63 provided in the environmental tester 61 and an ozone monitor 65 connected to the environmental tester 61 through a circulating channel forming member 66 was produced, as shown in FIG. 7. The ozone generator 63 was configured such that a xenon excimer lamp (manufactured by USHIO INC.) having a center wavelength of 172 nm and an input power of 20 W was disposed in a right-circular-cylindrical air flow channel forming member made of aluminum along a tube axis of the air flow channel forming member (see FIG. 3). As the ozone monitor 65, an ultraviolet ray-adsorption ozone monitor "EG-3000D" (manufactured by EBARA JITSUGYO CO., LTD.) was adopted. In the sterilization treatment mechanism for experiment (1), a gas (air) constituting the internal atmosphere of the environmental tester 61 was circulated through a circuit of the circulating channel forming member 66, and the ozone concentration in the air constituting the internal atmosphere was measured by the ozone monitor 65.

In the sterilization treatment mechanism for experiment (1), a sterilization treatment was performed by the sterilization method of the present invention.

A sterilization treatment mechanism for comparison experiment (hereinafter referred to as "sterilization treatment mechanism for experiment (2)") in which a discharge-type ozone generator having an input power (power consumption) of 45 W "GO ONE 1000T (type: GWD-1000T)" (manufactured by OHNIT CO., LTD.) was used as the ozone generator 63 in the sterilization treatment mechanism for experiment (1) was produced.

In the sterilization treatment mechanism for experiment (2), a production method of ozone through electrical discharge was adopted wherein ozone was produced by occurrence of silent discharge such as creeping discharge in the atmosphere of an air. Hereinafter, a sterilization method using an ozone-containing air obtained by the production method of ozone through electrical discharge which was performed in the sterilization treatment mechanism for experiment (2) is also referred to as "sterilization method through electrical discharge."

Figure 8:
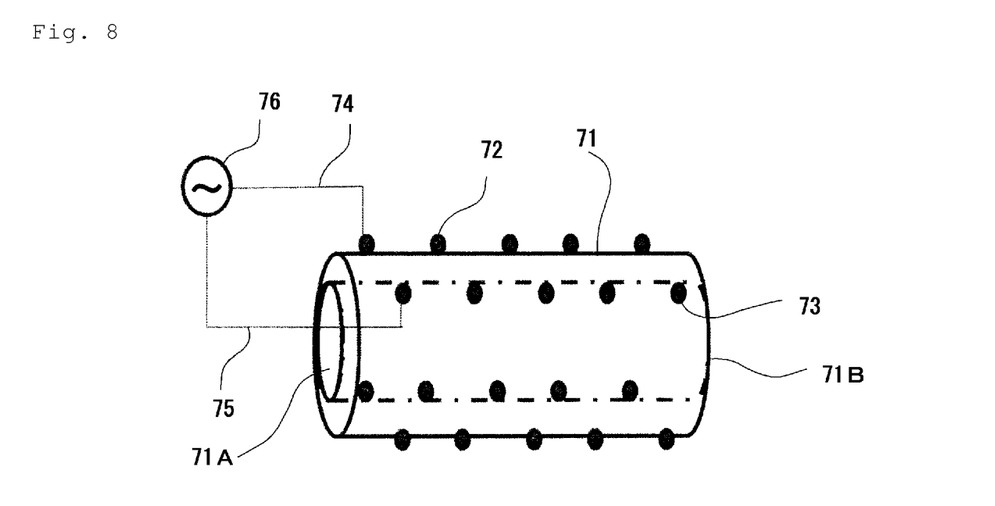
FIG. 8 is an explanatory view illustrating a main portion of an ozone generator constituting a sterilization treatment mechanism for comparison used in Experimental Example 1.

The ozone generator used in the production method of ozone through electrical discharge was provided with a right-circular-cylindrical air flow channel forming member 71 made of a dielectric material such as quartz glass, for example, as shown in FIG. 8. An air flow channel which allowed the air to flow from one end 71A to the other end 71B and allowed electrical discharge (silent discharge) to occur was formed by a cylindrical space formed by the inner circumferential surface of the air flow channel forming member 71. In the air flow channel forming member 71, one electrode 72 which helically extended along the tube axis was provided on the circumference surface, and the other electrode 73 which helically extended along the tube axis was provided on the inner circumferential surface. The electrodes 72 and 73 were connected to a high frequency power supply 76 through feeder wires 74 and 75, respectively.

On the other hand, a plurality of petri dishes for test and control were prepared. The petri dishes for test and control were filled with an agar medium, and $E.\ coli$ strain K12

(NBRC106373) was inoculated in the agar medium. In each of the petri dishes for test and control, the number of inoculated *E. coli* strain K12 (NBRC106373) was not lower than 1,000 and not more than 1,200.

In the produced sterilization treatment mechanisms for experiment (1) and (2), the ozone generator 63 was continuously driven under a condition where the relative humidity in the environmental tester 61 was 20% RH, 40% RH, 60% RH or 80% RH so that the ozone concentration in the environmental tester 61 was 40 ppm. In the environmental tester 61, a temperature was 20° C. and an air pressure was the same as atmospheric pressure. A door (not shown) of the environmental tester 61 was opened, the petri dishes for test were placed in the environmental tester 61, and the door was closed immediately. Due to opening and closing of the door of the environmental tester 61, the ozone concentration in the environmental tester 61 was decreased to 30 ppm. After that, the ozone concentration in the environmental tester 61 was maintained to 30±2 ppm by controlling the driving of the ozone generator 63 (ON/OFF). In the environmental tester 61 in which the controlled ozone concentration was 30±2 ppm, the temperature and pressure were constant. Thus, the *E. coli* strain K12 (NBRC106373) was exposed to the ozone-containing air having the ozone concentration of 30±2 ppm.

When an exposure time at which a CT value was 40, 60, 80 or 100 elapsed, the petri dishes for test were taken from the environmental tester 61. The petri dishes for test and the petri dishes for control were allowed to stand for 24 hours at a temperature of 37° C. for cultivation.

After the cultivation for 24 hours, the petri dishes for test and the petri dishes for control were observed.

In the sterilization treatment mechanism for experiment (1), the petri dishes were exposed to the ozone-containing air under a condition where the relative humidity in the environmental tester was 20% RH. In this case, there were 331 colonies in the petri dishes for test in which the CT value was 40. As the CT value was increased in an order of 60, 80 and 100, the number of colonies was decreased. There were 51 colonies in the petri dishes for test in which the CT value was 100.

In the sterilization treatment mechanism for experiment (1), the petri dishes were exposed to the ozone-containing air under a condition where the relative humidity in the environmental tester was 40% RH. In this case, there were 343 colonies in the petri dishes for test in which the CT value was 40. As the CT value was increased in an order of 60, 80 and 100, the number of colonies tended to be decreased. There were 16 colonies in the petri dishes for test in which the CT value was 100.

In the sterilization treatment mechanism for experiment (1), the petri dishes were exposed to the ozone-containing air under a condition where the relative humidity in the environmental tester was 60% RH. In this case, there were 267 colonies in the petri dishes for test in which the CT value was 40. As the CT value was increased in an order of 60, 80 and 100, the number of colonies was decreased. There were 18 colonies in the petri dishes for test in which the CT value was 100.

In the sterilization treatment mechanism for experiment (1), the petri dishes were exposed to the ozone-containing air under a condition where the relative humidity in the environmental tester was 80% RH. In this case, there were 77 colonies in the petri dishes for test in which the CT value was 40. As the CT value was increased in an order of 60, 80 and 100, the number of colonies was decreased. There were 13 colonies in the petri dishes for test in which the CT value was 100.

On the other hand, in the sterilization treatment mechanism for experiment (2), the petri dishes for test were exposed to the ozone-containing air under a condition where the relative humidity in the environmental tester was 20% RH. In all the petri dishes for test, there were not lower than 1,000 colonies.

In the sterilization treatment mechanism for experiment (2), the petri dishes were exposed to the ozone-containing air under a condition where the relative humidity in the environmental tester was 40% RH. In this case, there were not lower than 1,000 colonies in the petri dishes for test in which the CT value was 40. When the CT value was 60, 80 or 100, however, there were lower than 400 colonies and there were 186 colonies in the petri dishes for test in which the CT value was 100.

In the sterilization treatment mechanism for experiment (2), the petri dishes were exposed to the ozone-containing air under a condition where the relative humidity in the environmental tester was 60% RH. In this case, there were 185 colonies in the petri dishes for test in which the CT value was 40. As the CT value was increased in an order of 60, 80 and 100, the number of colonies was decreased. There were 86 colonies in the petri dishes for test in which the CT value was 100.

In the sterilization treatment mechanism for experiment (2), the petri dishes were exposed to the ozone-containing air under a condition where the relative humidity in the environmental tester was 80% RH. In this case, there were 81 colonies in the petri dishes for test in which the CT value was 40. As the CT value was increased in an order of 60, 80 and 100, the number of colonies was decreased. There were 3 colonies in the petri dishes for test in which the CT value was 100.

In all the petri dishes for control, there were not lower than 1,000 colonies.

Figure 9:
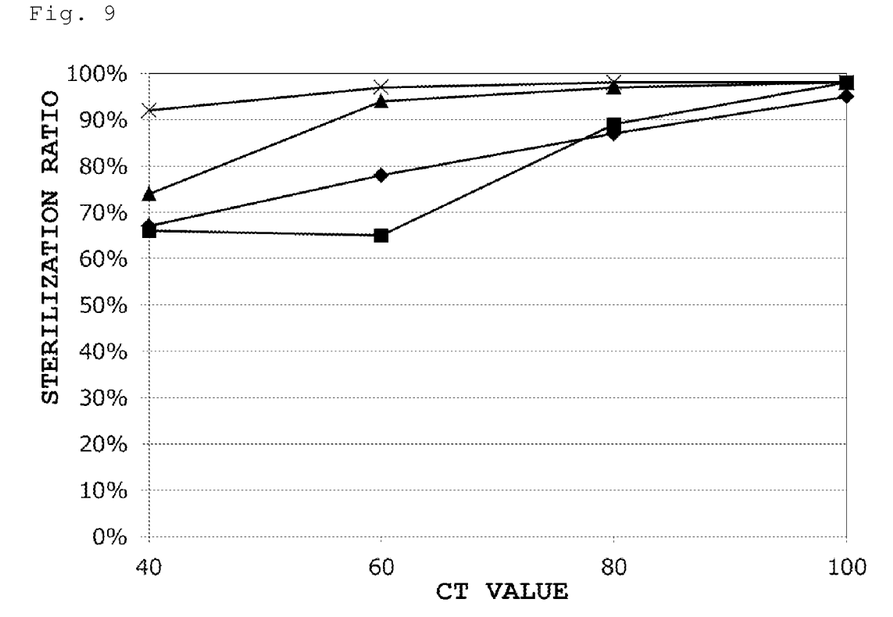
FIG. 9 is a graph showing a relationship between a CT value and a sterilization ratio which is obtained using the sterilization treatment mechanism for experiment in Experimental Example 1.
Figure 10:
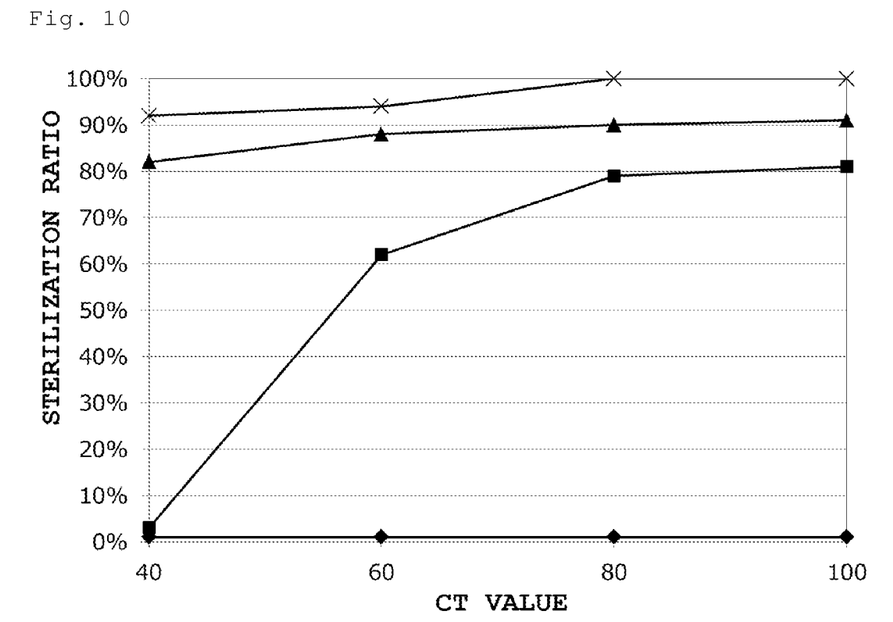
FIG. 10 is a graph showing a relationship between a CT value and a sterilization ratio which is obtained using the sterilization treatment mechanism for comparison experiment in Experimental Example 1.

In the petri dishes for test in which there were lower than 1,000 colonies, the sterilization ratio of the *E. coli* strain K12 (NBRC106373) was calculated from the number of the colonies. The results are shown in FIGS. 9 and 10. In FIGS. 9 and 10, the results under the condition where the relative humidity in the environmental tester was 20% RH were plotted by a mark of solid rhombus (♦) the results under the condition where the relative humidity in the environmental tester was 40% RH were plotted by a mark of solid square (■), the results under the condition where the relative humidity in the environmental tester was 60% RH were plotted by a mark of solid triangle (▲), and the results under the condition where the relative humidity in the environmental tester was 80% RH were plotted by a mark of cross (X).

As apparent from the results of Experimental Example 1, a high sterilization ratio of not lower than 65% is obtained in the sterilization treatment mechanism for experiment (1) even when an air having a relative humidity of 20% RH, 40% RH, 60% RH or 80% RH is used as a raw material air. In particular, it is clear that a high sterilization ratio is obtained even when an air having a relative humidity of not more than 60% RH, in which the sterilization effect or high sterilization ratio is not obtained in the sterilization treatment mechanism for experiment (2), is used as a raw material air.

Therefore, according to the sterilization treatment mechanism for experiment (1) in the present invention, that is, according to the sterilization method of the present invention, a sterilization treatment can be performed with high sterilization efficiency using ozone produced from an air regardless of the humidity of the air as an ozone raw material gas.

Specifically, in the sterilization treatment mechanism for experiment (2), that is, a sterilization method through electrical discharge, even when the CT value is 40, 60, 80 or 100 at a relative humidity of the raw material air of 80% RH or 60% RH, a high sterilization ratio of not lower than 75% is obtained. However, when the CT value is 40, the sterilization ratio is significantly low with the raw material air having a relative humidity of 40% RH. Even when the CT value is 40, 60, 80 or 100, the sterilization ratio is significantly low with the raw material air having a relative humidity of 20% RH.

Therefore, when the raw material air has low humidity in the sterilization method through electrical discharge, it is confirmed that the sterilization effect is not obtained or a sufficient sterilization efficiency is not obtained.

On the other hand, in the sterilization treatment mechanism for experiment (1), that is, the sterilization method of the present invention, it is apparent that a high sterilization ratio of not lower than 65% is obtained regardless of the relative humidity of the raw material air, unlike the sterilization treatment mechanism for experiment (2). Furthermore, when the CT value is 60, 80 or 100, a higher sterilization ratio is obtained with the raw material air having a relative humidity of 60% RH as compared with the sterilization treatment mechanism for experiment (2). When the CT value is 40, 60, 80 or 100, a higher sterilization ratio is obtained with the raw material air having a relative humidity of 20% RH or 40% RH as compared with the sterilization treatment mechanism for experiment (2).

Therefore, it is confirmed that sufficient sterilization efficiency is obtained regardless of the humidity of the raw material air in the sterilization method of the present invention.

A reason of large difference of sterilization efficiency caused by the humidity of the raw material air between the sterilization method of the present invention and the sterilization method through electrical discharge is not necessarily clear. However, the reason is estimated as follows.

It would be considered that each ozone-containing air obtained from an air by the production method of ozone through a photochemical reaction and the production method of ozone through electrical discharge contains radicals and ions derived from oxygen and hydrogen which are generated during production of ozone, in addition to ozone. The radicals and ions contained in the ozone-containing air are considered to be different depending on the process (photochemical reaction or electrical discharge) of the production method of ozone. Specifically, in the production method of ozone through a photochemical reaction, when the raw material air is irradiated with the light for producing ozone even in a low humidity environment, water (moisture) present in the raw material air is converted into droplets, from which radicals may be generated. On the other hand, in the production method of ozone through electrical discharge, even when water present in the raw material air is converted into droplets, radicals are not generated therefrom. Therefore, it is considered that radicals and ions contained in the ozone-containing air have an influence on the sterilization effect of the ozone-containing air and this influence causes the difference in sterilization efficiency.

Further, an experiment was performed in the same manner as in Experimental Example 1 except that in Experimental Example 1, the exposure time at which *E. coli* strain K12 (NBRC106373) inoculated in the petri dishes for test was exposed to the ozone-containing air was made constant and the ozone concentration in the ozone-containing air was changed so as to change the CT value to 40, 60, 80 or 100. The same results as in Experimental Example 1 were obtained in this experiment.

REFERENCE SIGNS LIST 10 excimer lamp
11 light-emitting tube
11A sealing portion
11B exhaust duct remaining portion
14 internal electrode
15 internal lead
16 metal foil
17 external lead for internal electrode
18 external electrode
19 external lead for external electrode
21 base member
22, 23 feeder wire
24 high frequency power supply
30 first sterilization treatment mechanism
31 partition
32 opening for air supply
40 ozone generator
41 air flow channel forming member
41A air inlet
41B air outlet
42 air introducing channel forming member
43 air leading channel forming member
43A air outlet
46 raw material air supply unit
50 second sterilization treatment mechanism
52 third sterilization treatment mechanism
54 fourth sterilization treatment mechanism
61 environmental tester
63 ozone generator
65 ozone monitor
66 circulating channel forming member
71 air flow channel forming member
71A one end
71B other end
72, 73 electrode
74, 75 feeder wire
76 high frequency power supply
S1 space where object to be sterilized exists
S2 space where ozone is produced
G1 raw material air
G2 ozone-containing air

The invention claimed is:

1. A sterilization method comprising:
    irradiating an air serving as an ozone raw material gas with light for producing ozone which does not include light with a wavelength region where the light decomposes ozone and which has a wavelength of about 172 nm to not more than 200 nm, to obtain an ozone-containing air; and
    exposing an object to be sterilized to the ozone-containing air, thereby subjecting the object to a sterilization treatment, wherein
    the ozone raw material gas has a relative humidity of 20% RH to not more than 60% RH.

2. The sterilization method according to claim 1, wherein the object to be sterilized exists in an opened space and the ozone is contained in the opened space in a concentration of not more than 100 ppm.

3. The sterilization method according to claim 2, wherein the object to be sterilized is exposed to the ozone-containing air by supplying the ozone-containing air to a space where the object to be sterilized exists, with the ozone-containing air obtained by irradiating the ozone raw material gas with the light for producing ozone in a space where ozone is produced.

4. The sterilization method according to claim 1, wherein the object to be sterilized is exposed to the ozone-containing air by supplying the ozone-containing air to a space where the object to be sterilized exists, with the ozone-containing air obtained by irradiating the ozone raw material gas with the light for producing ozone in a space where ozone is produced.

5. The sterilization method according to claim 4, wherein the space where ozone is produced is partitioned within the space where the object to be sterilized exists.

6. The sterilization method according to claim 5, wherein an air constituting an atmosphere of the space where the object to be sterilized exists is supplied as the ozone raw material gas in the space where ozone is produced.

7. The sterilization method of claim 1, wherein the relative humidity is 20% RH.

8. The sterilization method of claim 1, wherein the relative humidity is 20% RH to 40% and exposure of the object to be sterilized is at a CT value in a range of 40 to 80, the CT value determined as a product of the ozone concentration in parts per million and exposure time in minutes.

9. A sterilization method comprising:
introducing an air serving as an ozone raw material gas into an ozone generator, the ozone raw material gas having a relative humidity not less than 20% and not more than 60%;
irradiating the air ozone raw material gas with a xenon excimer lamp configured to generate light with a center wavelength of 172 nanometers to obtain an ozone-containing air; and
exposing an object to be sterilized to the ozone-containing air, thereby subjecting the object to a sterilization treatment.

10. The sterilization method according to claim 9, wherein the object to be sterilized exists in an opened space and the ozone is contained in the opened space in a concentration of not more than 100 ppm.

11. The sterilization method according to claim 10, wherein the object to be sterilized is exposed to the ozone-containing air by supplying the ozone-containing air to a space where the object to be sterilized exists, with the ozone-containing air obtained by irradiating the ozone raw material gas with the light for producing ozone in a space where ozone is produced.

12. The sterilization method according to claim 9, wherein the object to be sterilized is exposed to the ozone-containing air by supplying the ozone-containing air to a space where the object to be sterilized exists, with the ozone-containing air obtained by irradiating the ozone raw material gas with the light for producing ozone in a space where ozone is produced.

13. The sterilization method according to claim 12, wherein the space where ozone is produced is partitioned within the space where the object to be sterilized exists.

14. The sterilization method according to claim 13, wherein an air constituting an atmosphere of the space where the object to be sterilized exists is supplied as the ozone raw material gas in the space where ozone is produced.

15. The sterilization method of claim 9, wherein the relative humidity of the ozone raw material gas is not more than 40%.

16. The sterilization method of claim 9, wherein the relative humidity of the ozone raw material gas is in the range of 20% RH to 40% RH.

* * * * *